United States Patent [19]

Albarella et al.

[11] Patent Number: 4,563,417

[45] Date of Patent: Jan. 7, 1986

[54] NUCLEIC ACID HYBRIDIZATION ASSAY EMPLOYING ANTIBODIES TO INTERCALATION COMPLEXES

[75] Inventors: James P. Albarella, Elkhart, Ind.; Leslie H. D. Anderson, Encinitas, Calif.

[73] Assignee: Miles Laboratories, Inc., Elkhart, Ind.

[21] Appl. No.: 685,903

[22] Filed: Dec. 24, 1984

Related U.S. Application Data

[63] Continuation-in-part of Ser. No. 645,850, Aug. 31, 1984, abandoned, which is a continuation-in-part of Ser. No. 560,429, Dec. 12, 1983, abandoned.

[51] Int. Cl.[4] .................... C12Q 1/68; G01N 53/00; G01N 33/567
[52] U.S. Cl. .......................... 435/6; 435/7; 436/504; 935/77; 935/78
[58] Field of Search .............. 435/6, 7; 436/504; 935/77, 78

[56] References Cited

U.S. PATENT DOCUMENTS

| | | | |
|---|---|---|---|
| 4,257,774 | 3/1981 | Richardson et al. | 435/6 |
| 4,358,535 | 11/1982 | Falkow | 435/5 |
| 4,423,153 | 12/1983 | Ranney et al. | 436/63 |
| 4,493,899 | 1/1985 | Smith et al. | 435/6 |

FOREIGN PATENT DOCUMENTS

| | | | |
|---|---|---|---|
| 63879 | 11/1982 | European Pat. Off. | 435/6 |
| 70865 | 1/1983 | European Pat. Off. | 435/6 |
| 70867 | 1/1983 | European Pat. Off. | 435/6 |
| 1459 | 4/1983 | World Int. Prop. O. | 435/6 |
| 2286 | 7/1983 | World Int. Prop. O. | 435/6 |
| 2019408 | 10/1982 | United Kingdom | 435/6 |

OTHER PUBLICATIONS

Rudkin et al, Nature, 265 (1977) 472.
Poirier et al, Proc. Nat'l. Acad. Sci. USA, 79 (1981) 6443-7.

Primary Examiner—Christine M. Nucker
Attorney, Agent, or Firm—Andrew L. Klawitter

[57] ABSTRACT

Nucleic acid hybridization assay methods and reagent systems for detecting a particular polynucleotide sequence in a test medium. An aggregate is formed in the assay reaction mixture comprising intercalation complexes between a nucleic acid intercalator and double stranded nucleic acid associated with the hybridization product of the sequence to be detected and a nucleic acid probe sequence. Hybridization of the probe with the sequence to be detected can then be determined by addition of an antibody, or a fragment thereof, capable of binding with the intercalation complexes in the formed aggregate and measuring the antibody or fragment thereof which becomes bound to such intercalation complexes associated with hybridized probe. In one preferred embodiment, this method eliminates the need to chemically modify the probe in order to form a labeled reagent. In another embodiment, the method provides an advantageous method for labeling the probe by chemical modification.

43 Claims, 5 Drawing Figures

NUCLEIC ACID HYBRIDIZATION ASSAY EMPLOYING ANTIBODIES TO INTERCALATION COMPLEXES

CROSS-REFERENCE TO RELATED APPLICATIONS

This is a continuation-in-part of application Ser. No. 645,850, filed Aug. 31, 1984, which is a continuation-in-part of application Ser. No. 560,429, filed Dec. 12, 1983, both abandoned.

BACKGROUND OF THE INVENTION

1. Field of the Invention

This invention relates to nucleic acid hybridization assay methods and reagent systems for detecting specific polynucleotide sequences. The principle of nucleic acid hybridization assays was developed by workers in the recombinant DNA field as a means for determining and isolating particular polynucleotide base sequences of interest. It was found that single stranded nucleic acids, e.g., DNA and RNA, such as obtained by denaturing their double stranded forms, will hybridize or recombine under appropriate conditions with complementary single stranded nucleic acids. By labeling such complementary probe nucleic acids with some readily detectable chemical group, it was then made possible to detect the presence of any polynucleotide sequence of interest in a test medium containing sample nucleic acids in single stranded form.

In addition to the recombinant DNA field, the analytical hybridization technique can be applied to the detection of polynucleotides of importance in the fields of human and veterinary medicine, agriculture, and food science, among others. In particular, the technique can be used to detect and identify etiological agents such as bacteria and viruses, to screen bacteria for antibiotic resistance, to aid in the diagnosis of genetic disorders such as sickle cell anemia and thalassemia, and to detect cancerous cells. A general review of the technique and its present and future significance is provided in Biotechnology (August 1983), pp. 471-478.

2. Description of the Prior Art

The state-of-the-art nucleic acid hybridization assay technqiues involve chemical modification of either the probe nucleic acid or sample nucleic acids for the purpose of labeling and detection. The necessity of chemically modifying nucleic acids severely limits the practical use of the technique since it requires the large-scale preparation of labeled probes involving complicated and expensive synthetic and purification procedures or the in situ synthesis of labeled sample nucleic acids by the analytical user. In particular, the resulting labeled polynucleotide must retain the ability to hybridize efficiently with its complementary sample or probe sequence. Such a requirement severely limits the availability of useful synthetic approaches to label modification of polynucleotides intended for use in hybridization assays.

The early hybridization techniques involved the use of radioactive labels such as $^3H$, $^{32}P$, and $^{125}I$. Labeled probes are synthesized enzymatically from radiolabeled nucleotides and a polynucleotide by such techniques as nick translation, end labeling, second strand synthesis, reverse transcription, and transcription. Thus, an additional requirement of such enzymatic methods is that the modified or labeled nucleotides must serve as effective substrates for the polymerase enzymes involved in the assembly of the labeled polynucleotide. Direct chemical modification of the polynucleotide is also possible, however, such a method is quite inefficient in incorporating labels into the polynucleotide and can affect the ability of the polynucleotide to undergo hybridization.

Because of the handling and storage disadvantages of radiolabeled materials, there has been considerable continuing efforts to develop useful nonradioisotopic labeling approaches. Such labels have included light emitting molecules such as fluorescers and chemiluminescers, and ligand molecules which are capable of being specifically bound by counterpart binders which are in turn labeled with detectable chemical groups such as fluorescers and enzymes. Examples of ligand labels are haptens, which are specifically bound by antibodies, and other small molecules for which specific binding proteins exist, e.g., biotin which is bound by avidin.

British Pat. No. 2,019,408 describes polynucleotide probes which are labeled with biotin through cytochrome C linking groups and which are then detectable by enzyme-labeled avidin. An alternative approach to labeling probes with low molecular weight ligands such as biotin is described in European Pat. Appln. No. 63,879. In this technique, 5-allylamine-deoxyuridine triphosphate (dUTP) derivatives are condensed with the desired ligand label and the thus modified nucleotide is incorporated by standard enzymatic methods into the desired probe. The use of light emitting labels is suggested by European Pat. Appln. Nos. 70,685 and 70,687. Other representatives of the patent literature pertaining to hybridization assays are U.S. Pat. Nos. 4,302,204 concerning the use of certain water soluble polysaccharides to accelerate hybridization on a solid-phase; 4,358,535 concerning the detection of pathogens in clinical samples; and 4,395,486 concerning the detection of sickle cell anemia trait using a synthetic oligonucleotide probe.

Techniques for detecting directly the polynucleotide duplex formed as the product of hybridization between the sample and probe polynucleotides, and thereby dispensing with the chemical labeling of one or the other polynucleotide, have been generally unsuccessful. Attempts to generate antibodies which will selectively bind double stranded DNA/DNA hybrids over single stranded DNA have failed [Parker and Halloran, "Nucleic Acids in Immunology", ed. Plescia and Braun, Springer-Verlag, NY(1969) pp. 18 et seq]. Some success has been achieved in generating antibodies that will bind RNA/DNA mixed hybrids and have low affinity for the single stranded polynucleotides [Rudkin and Stollar, Nature 265:472(1977); Stuart et al, PNAS-(USA)78:3751(1981); Reddy and Sofer, Biochem. Biophys. Res. Commun. 103:959(1981); and Nakazato, Biochem. 19:2835(1980)], however, the sensitivity of these methods has not reached the levels required for clinical hybridization tests and one would have to use RNA probes which are well known to be quite unstable.

Accordingly, there is an established need for a technique for detecting hybridization without requiring chemical modification of polynucleotides or involving a labeling method of relative simplicity. Further, such technique should enable the use of a variety of labels, particularly of the nonradioisotopic type. A nucleic acid hybridization assay method and reagent system having these and other advantages are principal objectives of the present invention.

U.S. Pat. No. 4,257,774 describes a method for detecting various compounds that interact with nucleic acids, particularly compounds suspected as possible mutagens or carcinogens, by measuring the ability of such compounds to inhibit the binding of intercalators such as acridine orange to nucleic acids. Poirier, M.C. et al (1982) PNAS 79:6443-6447 describe the preparation of a monoclonal antibody selective for certain cis-platinum/double stranded DNA complexes over the free cis-platinum compound and double stranded DNA.

SUMMARY OF THE INVENTION

It has now been found that hybridization which occurs between sample nucleic acid and the probe in nucleic acid hybridization assays can be detected advantageously by means of an antibody, or an appropriate binding fragment thereof, capable of binding with intercalation complexes formed in association with hybridized probe. In essence, a particular polynucleotide sequence is detected in a test medium containing single stranded nucleic acids by forming a hybridization aggregate or product comprising hybridized probe and a nucleic acid intercalator compound bound to double stranded nucleic acid in the form of intercalation complexes. The antibody or fragment thereof is then used to detect intercalation complexes in the hybridization aggregate.

The use of nucleic acid hybridization as an analytical tool is based fundamentally on the double stranded, duplex structure of DNA. The hydrogen bonds between the purine and pyrimidine bases of the respective strands in double stranded DNA can be reversibly broken. The two complementary single strands of DNA resulting from this melting or denaturation of DNA will associate (also referred to as reannealing or hybridization) to reform the duplexed structure. As is now well known in the art, contact of a first single stranded nucleic acid, either DNA or RNA, which comprises a base sequence sufficiently complementary to (i.e., "homologous with") a second single stranded nucleic acid under appropriate solution conditions, will result in the formation of DNA/DNA, RNA/DNA, or RNA/RNA hybrids, as the case may be.

The present invention enables the detection of formed hybrids by inducing an immunogenic modification of double stranded nucleic acid in the region of hybridization or in flanking regions. The resulting product can then be detected by conventional assay schemes based on the binding of specific antibody to the epitopes or antigenic determinants formed on the hybridization product. The requisite immunogenic modification of double stranded nucleic acid is accomplished principally by binding of a molecule, usually a low molecular weight compound, to the duplex. Such binding results in the creation of an antigenic determinant which distinguishes double stranded nucleic acid from both single stranded nucleic acid and the free, unbound modifier molecule. Preferably, this is accomplished by employing a modifier compound which is essentially incapable of binding with single stranded nucleic acid and which forms a binding complex with double stranded nucleic acid which alters the normal helical relationship of the complementary strands of the duplex.

Such modifier molecule as described herein is a nucleic acid intercalator which preferentially will interact with the normal nucleic acid helix by a non-covalent insertion between base pairs. Such insertion causes, in this preferred interaction, the tertiary structure of the helix to change by unwinding and elongation along the helical axis. A schematic representation of this preferred intercalation interaction is shown in FIG. 1 of the drawings. The resulting intercalation complex is characterized by newly formed antigenic determinants which are understood to comprise the intercalated modifier compound and the reoriented phosphodiesterase backbones of the respective strands of the duplex.

Preferably, the intercalator compound is one of the generally planar, aromatic organic molecules known to form intercalation complexes with double stranded nucleic acid. Such compounds are exemplified by the acridine dyes, e.g., acridine orange, the phenanthridines, e.g., ethidium, the phenazines, furocoumarins, phenothiazines, quinolines, and the like as are more fully described below. It should be clearly understood that while the present invention will be hereinafter described with particular reference to such intercalator compounds, the present invention contemplates the use of equivalent modifier molecules which, as described above, will bind to double stranded nucleic acid to induce an immunogenic change in the duplex.

In accordance with the present invention, the intercalator can be combined with the test medium, and thereby become exposed to the double stranded nucleic acids present and/or forming in the hybridization reaction mixture, as a separate, free compound and bind noncovalently to such double stranded nucleic acids to form intercalation complexes. Alternatively, the intercalator can be appropriately linked by chemical bonds, preferably covalent bonds, to the probe. In the former case, the present invention provides a method for performing a hybridization assay without the need to chemically modify either the sample or probe polynucleotide in order to detect hybridization. In the latter case, a simple, synthetically straightforward means for labeling polynucleotides or the hybridization aggregate is provided by the use of photoreactable forms of the intercalator.

In all embodiments, the present invention provides a highly versatile, sensitive, and specific method for detecting hybridization based on antibody binding to the intercalation complexes in the aggregate formed. Of course, appropriate fragments and polyfunctional forms of the antibody can be used as described more fully below, and it will be understood that when used in this disclosure the term antibody will mean its fragmented and polyfunctional forms as well, unless otherwise noted. Determining the binding of antibody to intercalation complexes can be accomplished in a variety of conventional manners and preferably involves the use of antibody labeled with a detectable chemical group such as an enzymatically active group, a fluorescer, a luminescer, a specifically bindable ligand, or a radioisotope.

The invention is applicable to all conventional hybridization assay formats, and in general to any format that is possible based on formation of a hybridization product or aggregate comprising double stranded nucleic acid. In particular, the unique detection scheme of the present invention can be used in solution and solid-phase hybridization formats, including, in the latter case, formats involving immobilization of either sample or probe nucleic acids and sandwich formats.

The hybridization product or aggregate formed according to the present invention comprises hybridized probe and intercalator bound to double stranded nucleic acid in the form of intercalation complexes. The intercalation complexes can involve double stranded regions formed by hybridization between sample and probe nucleic acids. Alternatively, such double stranded regions can be comprised in the probe itself and in such case can additionally be intercalated prior to use of the probe in the assay. Thus, the detectable intercalation complexes can be formed in situ during the assay or can be existent in the probe reagent as present to the test medium. Further, the intercalation complexes can be chemically linked to one or both of the strands of the intercalated duplex. In general, any variation can be followed provided that the hybridization product ultimately comprise intercalation complexes detectable by the antibody binding phenomenon which is the underlying basis of the present invention.

Thus, the present invention provides an advantageous nucleic acid hybridization method and reagent system. Additionally, there is provided a novel antibody reagent capable of binding with intercalation complexes. Furthermore, besides the detection of particular polynucleotide sequences, the present invention provides a general method for detecting double stranded nucleic acid by adding intercalator and the anti-(intercalation complex) antibody and determining antibody binding.

The advantages of the present invention are significant and many. The invention is amenable to a wide variety of nonradioactive detection methods. Further, labeling of nucleic acids is straightforward and uses easily synthesized reagents. Labeling with the intercalator does not require expensive polymerases, and the labeling density of the intercalator can be easily controlled. Certain preferred embodiments have other advantages. In those embodiments in which the intercalator-nucleic acid complex is formed in situ, no prior synthesis of the complex is required and this approach can be used in a format in which a probe is immobilized on a solid support and immersed in a solution containing the specimen nucleic acid. In the embodiment where the intercalator is covalently coupled to the nucleic acid, the intercalator is attached to the probe during the manufacturing process, resulting in a controlled level of saturation. This approach also minimizes user exposure to an intercalating agent, many of which may be potentially hazardous.

DESCRIPTION OF THE PREFERRED EMBODIMENTS

Intercalator

Figure 1:
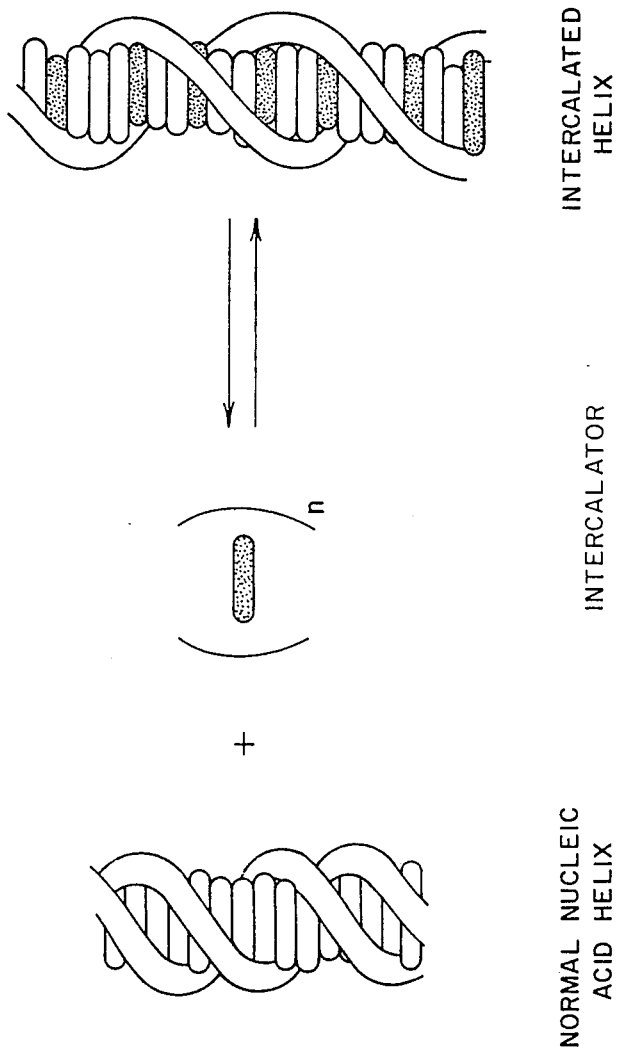
FIG. 1, as described above, is a schematic representation of the preferred interaction between intercalator and double stranded nucleic acid which results in an intercalation complex that is detectable by antibody.

As described above, the intercalator compound preferably is a low molecular weight, planar, usually aromatic but sometimes polycyclic, molecule capable of binding with double stranded nucleic acids, e.g., DNA/DNA, DNA/RNA, or RNA/RNA duplexes, usually by insertion between base pairs. The primary binding mechanism will usually be noncovalent, with covalent binding occuring as a second step where the intercalator has reactive or activatable chemical groups which will form covalent bonds with neighboring chemical groups on one or both of the intercalated duplex strands. The result of intercalation is the spreading of adjacent base pairs to about twice their normal separation distance, leading to an increase in molecular length of the duplex. Further, unwinding of the double helix of about 12 to 36 degrees must occur in order to accomodate the intercalator. General reviews and further information can be obtained from Lerman, J. Mol. Biol. 3:18(1961); Bloomfield et al, "Physical Chemistry of Nucleic Acids", Chapter 7, pp. 429-476, Harper and Rowe, NY(1974); Waring, Nature 219:1320 (1968); Hartmann et al, Angew. Chem., Engl. Ed. 7:693(1968); Lippard, Accts. Chem. Res. 11:211(1978); Wilson, Intercalation Chemistry(1982), 445; and Berman et al, Ann. Rev. Biophys. Bioeng. 10:87(1981).

A wide variety of intercalating agents can be used in the present invention. Some classes of these agents and examples of specific compounds are given in the following table:

| Intercalator Classes and Representative Compounds | Literature References |
| --- | --- |
| A. Acridine dyes | Lerman, supra; Bloomfield et al, supra; |
| proflavin, acridine orange, quinacrine, acriflavine | Miller et al, Biopolymers 19:2091(1980) |
| B. Phenanthridines | Bloomfield et al, supra; Miller et al, supra |
| ethidium | |
| coralyne | Wilson et al, J. Med. Chem. 19:1261(1976) |
| ellipticine, ellipticine cation and derivatives | Festy et al, FEBS Letters 17:321(1971); Kohn et al, Cancer Res. 35:71(1976); LePecq et al, PNAS (USA)71: 5078(1974); Pelaprat et al, J. Med. Chem. 23:1330(1980) |
| C. Phenazines | Bloomfield et al, supra |
| 5-methylphenazine cation | |
| D. Phenothiazines | " |
| chlopromazine | |
| E. Quinolines | " |
| chloroquine | |
| quinine | |
| F. Aflatoxin | " |
| G. Polycyclic hydrocarbons and their oxirane derivatives | " |
| 3,4-benzpyrene benzopyrene diol oxirane 82:929(1978) | Yang et al, Biochem. Biophys. Res. Comm. |
| benzanthracene-5,6-oxide | Amea et al, Science 176:47(1972) |
| H. Actinomycens | Bloomfield et al, supra |
| actinomycin D | |
| I. Anthracyclinones | " |
| β-rhodomycin A | |
| daunamycin | |
| J. Thiaxanthenones | " |
| miracil D | |
| K. Anthramycin | " |
| L. Mitomycin | Ogawa et al, Nucl. Acids Res., Spec. Publ. 3:79(1977); Akhtar et al, Can. J. Chem. 53:2891(1975) |
| M. Platinium Complexes | Lippard, supra |
| N. Polyintercalators echinomycin | Waring et al, Nature 252:653(1974); Wakelin, Biochem. J. 157:721(1976) |
| quinomycin triostin BBM928A tandem | Lee et al, Biochem. J. 173:115(1971); Huang et al, Biochem. 19: 5537(1980); Viswamitra et al, Nature 289: 817(1981) |

| Intercalator Classes and Representative Compounds | Literature References |
|---|---|
| diacridines | LePecq et al, PNAS (USA)72:2915(1975); Carrellakis et al, Biochem. Biophys. Acta 418:277(1976); Wakelin et al, Biochem 17:5057(1978); Wakelin et al, FEBS Lett. 104:261(1979); Capelle et al, Biochem. 18:3354(1979); Wright et al, Biochem. 19:5825(1980); Bernier et al Biochem. J. 199:479(1981); King et al, Biochem. 21: 4982(1982) |
| ethidium dimer | Gaugain et al, Biochem. 17:5078(1978); Kuhlman et al, Nucl. Acids Res. 5:2629 (1978); Marlcovits et al, Anal. Biochem. 94:259(1979); Dervan et al, JACS 100:1968 (1978); ibid 101: 3664(1979). |
| ellipticene dimers and analogs | Debarre et al, Compt. Rend. Ser. D 284: 81(1977); Pelaprat et al, J. Med. Chem. 23:1336(1980) |
| heterodimers | Cain et al, J. Med. Chem. 21:658(1978); Gaugain et al, Biochem. 17:5078(1978) |
| trimers | Hansen et al, JCS Chem. Comm. 162(1983); Atnell et al, JACS 105: 2913(1983) |
| O. Norphillin A | Loun et al, JACS 104: 3213(1982) |
| P. Fluorenes and fluorenones fluorenodiamines | Bloomfield et al, supra Witkowski et al, Wiss. Beitr.-Martin-Luther-Univ. Halle Wittenberg, 11(1981) |
| Q. Furocoumarins angelicin | Venema et al, MGG, Mol. Gen. Genet. 179;1 (1980) |
| 4,5'-dimethylangelicin | Vedaldi et al, Chem.-Biol. Interact. 36: 275(1981) |
| psoralen | Marciani et al, Z. Naturforsch B 27(2): 196(1972) |
| 8-methoxypsoralen | Belognzov et al, Mutat. Res. 84:11(1981); Scott et al, Photochem. Photobiol. 34:63(1981) |
| 5-aminomethyl-8-methoxypsoralen | Hansen et al, Tet. Lett 22:1847(1981) |
| 4,5,8-trimethylpsoralen | Ben-Hur et al, Biochem. Biophys. Acta 331:181(1973) |
| 4'-aminomethyl-4,5,8-trimethylpsoralen | Issacs et al, Biochem. 16:1058(1977) |
| xanthotoxin | Hradecma et al, Acta Virol. (Engl. Ed.) 26:305(1982) |
| khellin | Beaumont et al, Biochem. Biophys. Acta 608:1829(1980) |
| R. Benzodipyrones | Murx et al, J. Het. Chem. 12:417(1975); Horter et al, Photochem. Photobiol. 20: 407(1974) |
| S. Monostral Past Blue | Juarranz et al, Acta Histochem. 70:130 (1982) |

Several embodiments of the present invention involve the chemical, e.g., covalent, linkage of the intercalator to one or both of the complementary strands of a duplex. Essentially any convenient method can be used to accomplish such linkage. Conveniently, the linkage is formed by effecting intercalation with a reactive, preferably photoreactive intercalator, followed by the linking reaction. A particularly useful method involves the use of azidointercalators. The reactive nitrenes are readily generated at long wavelength ultraviolet or visible light and the nitrenes of arylazides prefer insertion reactions over their rearrangement products [see White et al, Methods in Enzymol. 46:644(1977)]. Representative azidointercalators are 3-azidoacridine, 9-azidoacridine, ethidium monoazide, ethidium diazide, ethidium dimer azide [Mitchell et al, JACS 104:4265(1982)], 4-azido-7-chloroquinoline, and 2-azidofluorene. Other useful photoreactable intercalators are the furocoumarins which form [2+2] cycloadducts with pyrimidine residues. Alkylating agents can also be used such as bis-chloroethylamines and epoxides or aziridines, e.g., aflatoxins, polycyclic hydrocarbon epoxides, mitomycin, and norphillin A.

Depending on the hybridization format involved, as will be described in detail below, chemically linked intercalation complexes can be used in a variety of manners in the present invention. They can be formed in situ in the hybridization reaction mixture or in a process step thereafter, or can be a step in the synthesis of a labeled probe or sample nucleic acid. In the latter case, where intercalation occurs in the region of complementarity between the probe and sample nucleic acids, mono-linkages will be accomplished followed by denaturing of such region to yield single stranded nucleic acid with chemically linked intercalator oriented such that upon hybridization, the linked intercalator will assume an intercalation position.

HYBRIDIZATION FORMATS AND PROBES

The probe will comprise at least one single stranded base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear, or they can be self-complementary and form hairpin loops. In addition, the homologous region of the probe can be flanked at the 3'- and 5'-terminii by non-homologous sequences, such as those comprising the DNA or RNA of a vector into which the homologous sequence had been inserted for propagation. In either instance, the probe as presented as an analytical reagent will exhibit detectable hybridization at one or more points with sample nucleic acids of interest. Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA. Particularly preferred will be linear or circular probes wherein the homologous probe sequence is in essentially only single stranded form [see particularly, Hu and Messing, Gene 17:271-277(1982)].

Where the probe is used in a hybridization format calling for use of an intercalator-labeled probe, as will be seen below, such probe can be in a variety of forms such as a completely single stranded polynucleotide having intercalator chemically linked thereto whereby hybridization results in formation of intercalation complexes. Alternatively, the probe can comprise a double stranded portion or portions which have been intercalated, optionally with covalent linkage of the intercalator to one or both strands in the duplex.

In terms of hybridization formats, the present invention is focused on formation of a hybridization aggregate comprising the hybridized probe and the intercalator bound to duplexes in the form of the antibody-detectable intercalation complexes. Thus, the event of hybridization is associated with the formation of the detectable intercalation complexes. Fundamentally, the resulting intercalation complexes in the aggregate can be in the region of hybridization between the sample and probe nucleic acids or can be in a double stranded region remote from the hybridization region. In such latter case, the intercalated region can be formed during the assay or can be in the intercalated state when brought to the assay, e.g., covalently linked or noncovalently intercalated double stranded regions serving as labels for the probe.

Practice of the present analytical method is not limited to any particular hybridization format. Any conventionl hybridization technique can be used. As improvements are made and as conceptually new formats are developed, such can be readily applied to carrying out the present method. Conventional hybridization formats which are particularly useful include those wherein the sample nucleic acids or the polynucleotide probe is immobilized on a solid support (solid-phase hybridization) and those wherein the polynucleotide species are all in solution (solution hybridization).

In solid-phase hybridization formats, one of the polynucleotide species participating in hybridization is fixed in an appropriate manner in its single stranded form to a solid support. Useful solid supports are well known in the art and include those which bind nucleic acids either covalently or noncovalently. Noncovalent supports which are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having chemically reactive groups or groups, such as dichlorotriazine, diazobenzyloxymethyl, and the like, which can be activated for binding to polynucleotides.

A typical solid-phase hybridization technique begins with immobilization of sample nucleic acids onto the support in single stranded form. This initial step essentially prevents reannealing of complementary strands from the sample and can be used as a means for concentrating sample material on the support for enhanced detectability. The polynucleotide probe is then contacted with the support and hybridization detected by antibody binding as described herein. The solid support provides a convenient means for separating antibody which binds to intercalation complexes associated with hybridized probe from that which does not so bind.

Another method of interest is the sandwich hybridization technique wherein one of two mutually exclusive fragments of the homologous sequence of the probe is immobilized and the other is labeled. The presence of the polynucleotide sequence of interest results in dual hybridization to the immobilized and labeled probe segments, again with the same ultimate measurement of support-associated intercalation complexes. See Methods in Enzymology 65:468(1980) and Gene 21:77-85(1983) for further details.

For purposes of better illustration, the following solid-phase hybridization methods are particularly useful in the present invention. Schematic diagrams of these basic methods are provided in the drawings.

Method type 1

Figure 2:
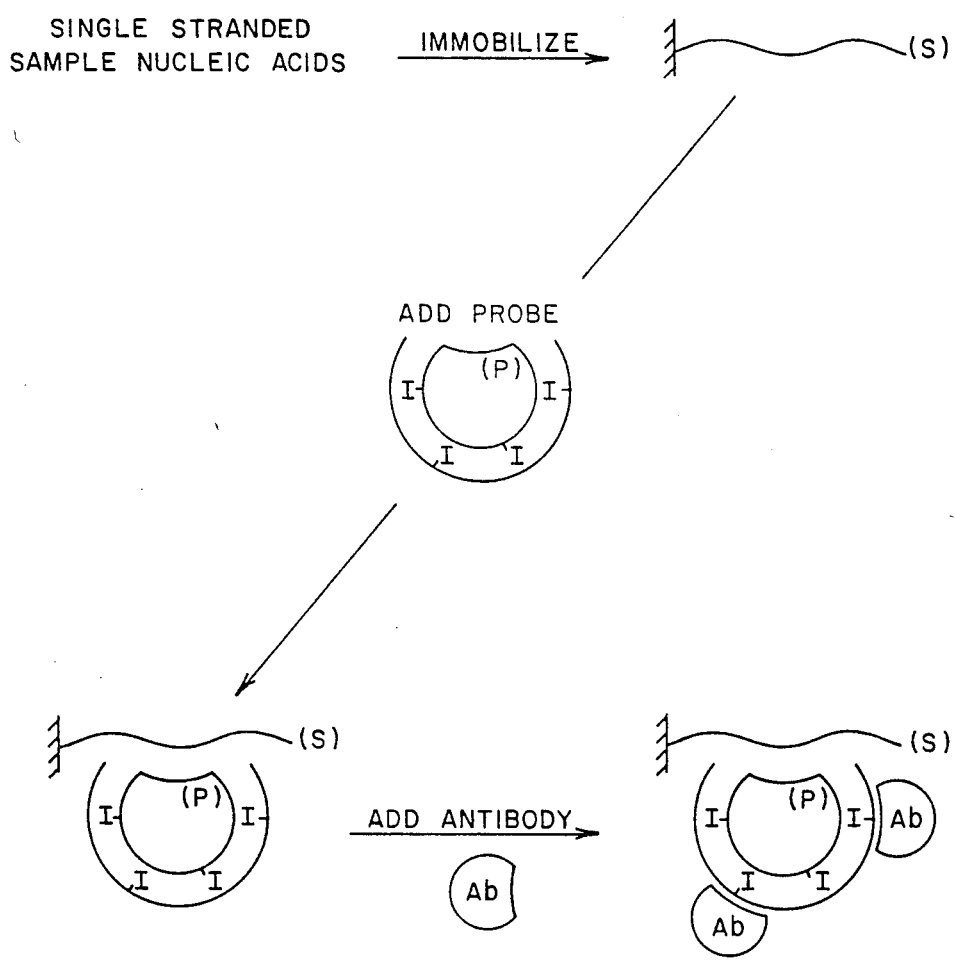
FIGS. 2-5 are schematic diagrams of four preferred hybridization formats for use in the present invention.

In this method, illustrated in FIG. 2, the single stranded nucleic acids from the liquid test medium are first immobilized on a solid support. A hybridization reaction mixture is then formed by contacting the immobilized sample nucleic acids (S) with the probe (P) which in this case comprises, in addition to the complementary single stranded portion, at least one double stranded portion which is chemically linked with the intercalator (I) in the form of intercalation complexes. A particularly useful form of the probe is the circular form described by Hu and Messing, supra. The resulting hybridization aggregate comprises the immobilized polynucleotide of interest hybridized with the probe which has a covalently linked, intercalculated double stranded region. The solid support carrying immobilized duplexes is then preferentially separated from the remainder of the reaction mixture. The antibody (Ab) is added, preferably labeled with a detectable group, and the resulting immobilized antibody bound to intercalation complexes in the aggregate is separated from the remainder of the reaction mixture. The antibody bound to the support is then determined to complete the assay. Alternatively, the antibody in the separated solution can be determined; although this will generally be less preferred since a large excess of antibody is normally used.

A variation of this method is to employ a probe such as above, but not having covalently linked intercalator bound to the double stranded region. Rather, the intercalator is added to the immobilized aggregate resulting in the formation of intercalator complexes in both the double stranded portion of the probe and the duplexed region formed by hybridization.

Method type 2

Figure 3:
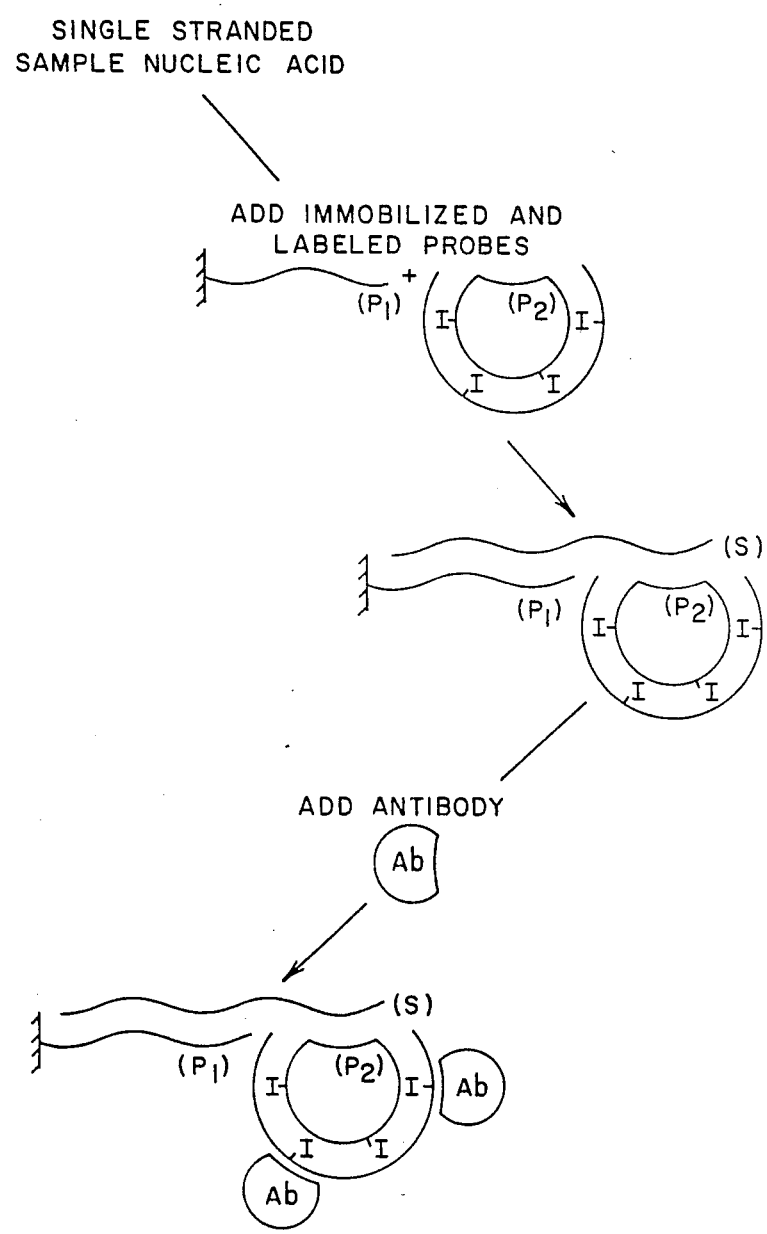

This is a sandwich format and is illustrated in FIG. 3. A reaction mixture is formed among the test medium containing the sequence of interest (S) and the first and second probes, each comprising respectively at least one base sequence complementary to a mutually exclusive portion of the sequence of interest. The first probe ($P_1$) is immobilized on a solid support and the second probe ($P_2$) is labeled with covalently linked, intercalation complexes as in Method type 1 above. The resulting hybridization aggregate comprises the sequence of interest hybridized to both the immobilized first probe and the intercalation complex-labeled second probe. The antibody is added, preferably in labeled form, and the resulting immobilized antibody bound to intercalation complexes in the aggregate is separated from the remainder of the reaction mixture. The bound antibody is determined to then complete the assay.

There are several useful variations of this method. First, as in the case of the variation of Method type 1, one can employ a probe which does not comprise covalently linked intercalator, but rather can add free intercalator to the immobilized aggregate resulting in the formation of intercalator complexes with all available double stranded regions. Also, as an alternative to using a second probe with a double stranded portion, one can use a probe of entirely single stranded nucleic acid with intercalator chemically linked thereto so that upon hybridization there are formed intercalation complexes, or with intercalator being added so that intercalation occurs between the duplexes formed between the two probes and the sequence to be detected.

Method type 3

Figure 4:
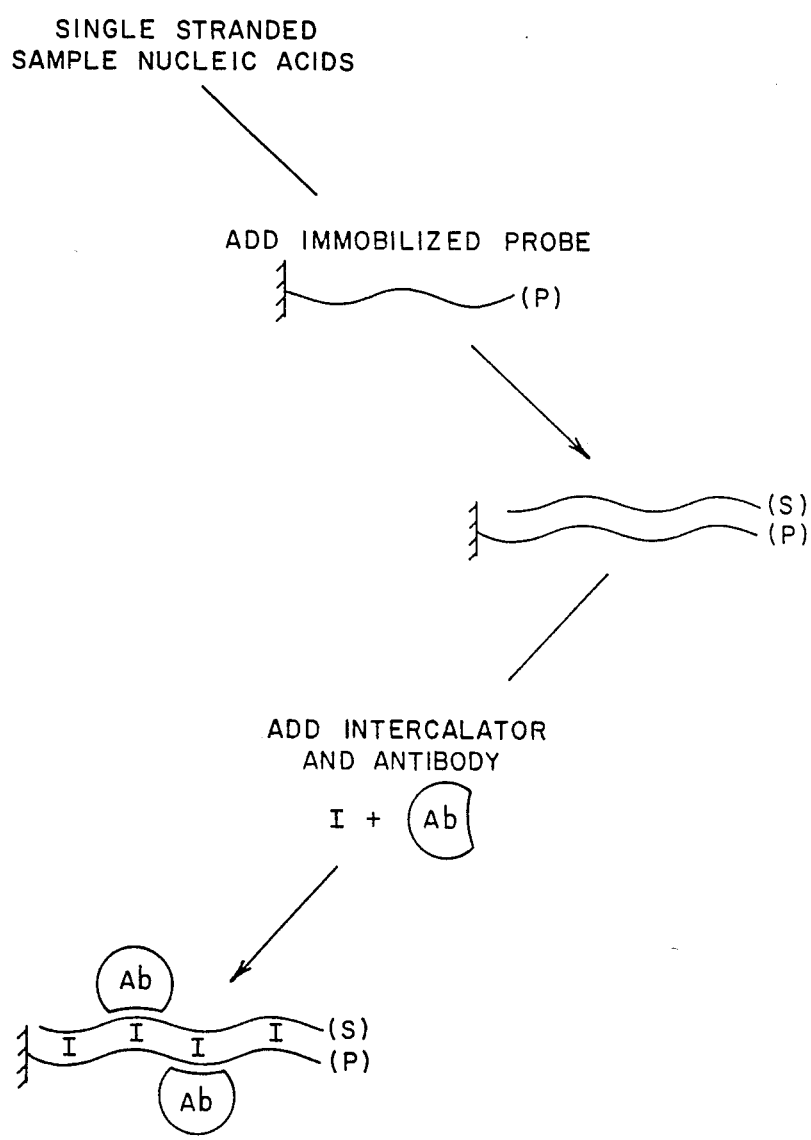

FIG. 4 illustrates a further preferred solid-phase format. The sample nucleic acids are contacted with immobilized probe and preferably the resulting immobilized duplexes are separated from the remainder of the reaction mixture. In this format, the probe is in single stranded form. The resulting hybridization product comprises the immobilized probe hybridized with the sequence of interest. Also, this format allows significant reannealing between complementary regions of sample nucleic acid which can take place on the immobilized aggregate. Such reannealing works to the advantages of the assay since it provides additional double stranded nucleic acid for subsequent intercalation. The next step in the assay is to add intercalator and the antibody, again preferably in a labeled form. The assay is completed by separation and antibody determination steps as in the previous formats.

Method type 4

Figure 5:
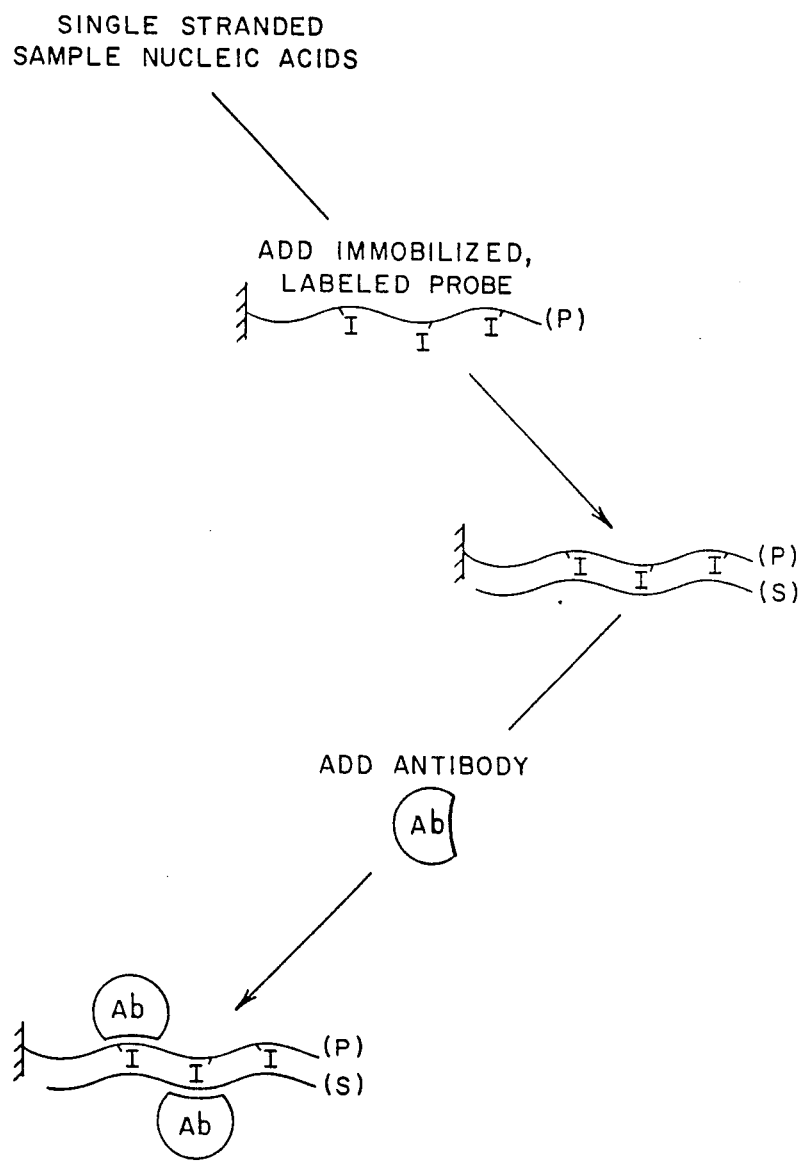

In this method, illustrated in FIG. 5, the single stranded sample nucleic acids are contacted with immobilized probe where, in this case, such probe is chemically linked, e.g., covalently, to the intercalator such that duplex formation in the region of the linked intercalator results in formation of intercalation complexes. This is a highly advantageous format in that it is the only known technique wherein the probe is both immobilized and labeled, requiring no immobilization or labeling step to be performed at the time of the assay. The resulting aggregate comprises covalently linked, intercalation complexes in the region of hybridization between sample and probe nucleic acids and in any reannealed sample regions. Antibody is then added and the assay completed as in the previous formats. This format provides the advantage of eliminating the need for the analyst to handle solutions of the free intercalator which in some cases can be potentially hazardous. A simple variation of this technique is to immobilize sample nucleic acids rather than the labeled probe and proceed in the normal fashion. This is somewhat less advantageous but is a practical assay approach.

A variety of solution-phase hybridization formats can also be applied to the present invention. Such formats are characterized by the feature that the hybridization step involves soluble forms of both the sample nucleic acids and the probe. This can result in significantly faster hybridizations since the kinetics are much faster when both strands are in solution compared to when on is immobilized. Normally, subsequent to the hybridization step, the resulting hybrids are rendered immobile for purposes of detection. Such immobilization can be accomplished in a variety of ways. Conventionally it is known to selectively immobilize cuplexes by exposure to adsorbents such as hydroxyapatite and nitrocellulose membranes.

A particularly useful approach to immobilizing hybrids formed from a solution-phase hybridization involves the use of a probe which comprises a binding site for a binding substance. After the hybridization step then, one can add an immobilized form of the binding substance which will effectively bind and immobilize the hybrids through the binding site on the probe. Such binding site can be present in a single stranded hybridizable portion of the probe or can be present as a result of a chemical modification of the probe. Examples of binding sites existing in the nucleotide sequence are where the probe comprises a promoter sequence (e.g., lac-promoter, trp-promoter) which is bindable by a promoter protein (e.g., bacteriophage promoters, RNA polymerase), or comprises an operator sequence (e.g., lac operator) which is bindable by a repressor protein (e.g., lac repressor), or comprises rare, antigenic nucleotides or sequences (e.g., 5-bromo or 5-iododeoxyuridine, Z-DNA) which are bindable by specific antibodies [see also British Pat. Spec. No. 2,125,964]. Binding sites introduced by chemical modification of the probe are particularly useful and normally involve linking one member of a specific binding pair to the probe nucleic acid. Useful binding pairs from which to choose include biotin/avidin, haptens and antigens/antibodies, MS-1320-CIP-II carbohydrates/lectins, enzymes/inhibitors, and the like. Where the binding pair consists of a proteinaceous member and a nonproteinaceous member, it will be preferred to link the nonproteinaceous member to the probe since the proteinaceous member may be unstable under the denaturing conditions of hybridization of the probe. Preferable systems involve linking the probe with biotin or a hapten and employing immobilized avidin or anti-hapten antibody, respectively. Preparation of useful ligand-labeled probes is known in the literature [Langer et al (1981) Proc. Natl. Acad. Sci. 78:6633; Broker (1978) Nucl. Acids Res. 5:363; Sodja et al (1978) Nucl. Acids Res. 5:385; Tchen et al (1984) Proc. Natl. Acad. Sci. 81:3466]. Immobilization of the binding substane can follow conventional techniques.

A large variety of methods are known for immobilizing proteins on solid supports and these methods are applicable to the immobilization of the binding substance [see Methods in Enzymology, Vol. 44(1976)]. Antibodies, for example, are immobilized either by covalent coupling or by noncovalent adsorption. Noncovalent methods frequently employed are adsorption to polystyrene beads or microparticles and to polyvinylchloride surface. Many covalent methods are used for immobilizing proteins and a few include cyanogen bromide activated agaroses and dextrans; glutaraldehyde activated nylons and polyacrylamides; and epoxides on acrylic and other supports.

The above illustrative methods are particularly preferred, however, the present invention is not limited to any particular hybridization format. Any approach to an assay can be followed provided that detectable intercalation complexes result in association with hybridization of the probe nucleic acid. For instance, in addition to the above methods, one can devise a solution phase hybridization format wherein a solid-phase antibody to intercalation complexes is employed to immobilize hybridized probe. There will be sufficient intercalation complexes formed in the hybridization product between sample and probe nucleic acids, the latter being in essentially only single stranded form, such that both solid-phase antibody and labeled antibody can bind. The amount of label associated with the solid-phase is then measured and is related to the presence of the sequence to be determined. Other useful formats will be evident to one of ordinary skill in the art.

ANTIBODY REAGENT AND DETECTION SCHEMES

A fundamental principle of the present invention is the ability to first bind an antibody, or a fragment or some other equivalent thereof, to the hybridization aggregate comprising hybridized probe and then to detect such antibody binding. As stated above, the antibody reagent can consist of whole antibodies, antibody fragments, polyfunctional antibody aggregates, or in general any substance comprising one or more intercalation complex-specific binding sites from an antibody. When in the form of whole antibody, it can belong to any of the classes and subclasses of known immunoglobulines, e.g., IgG, IgM, and so forth. Any fragment of any such antibody which retains specific binding affinity for intercalation complexes can also be employed, for instance, the fragments of IgG conventionally known as Fab, F(ab'), and F(ab')$_2$. In addition, aggregates, polymers, and conjugates of immunoglobulins or their fragments can be used where appropriate.

The immunoglobulin source for the antibody reagent can be obtained in any available manner such as conventional antiserum and monoclonal techniques. Antiserum can be obtained by well-established techniques involving immunization of an animal, such as a mouse, rabbit, guinea pig or goat, with an appropriate immunogen. The immunogen will usually comprise an ionic complex between a cationic protein or protein derivative (e.g., methylated bovine serum albumin) and the anionic intercalator-nucleic acid complex. Ideally, the intercalator should be covalently coupled to the double stranded nucleic acid. Alternatively, the intercalator-DNA conjugate can be covalently coupled to a carrier protein. The immunoglobulins can also be obtained by somatic cell hybridization techniques, such resulting in what are commonly referred to as monoclonal antibodies. The immunogen used for primary injections leading to hybridoma formation will be as described above.

The antibody reagent will be characterized by its ability to bind with an intercalation complex formed between a selected intercalator and double stranded nucleic acid in general without regard to the specific base sequences proximate to the site of intercalation. Furthermore, it will be substantially incapable of binding to single stranded nucleic acids or to free intercalator. As a result, antibody binding will occur only at intercalation complexes which by proper design of the assay format will be significantly present only in association with hybridized probe.

The binding of the antibody reagent to the hybridization aggregate in the present method can be detected by any convenient technique. Advantageously, the antibody reagent will itself be labeled with a detectable chemical group. Such detectable chemical group can be any material having a detectable physical or chemical property. Such materials have been well-developed in the field of immunoassays and in general most any label useful in such methods can be applied to the present invention. Particularly useful are enzymatically active groups, such as enzymes (see Clin. Chem. (1976)22:1243), enzyme substrates (see British Pat. Spec. 1,548,741), coenzymes (see U.S. Pat. Nos. 4,230,797 and 4,238,565), and enzyme inhibitors (see U.S. Pat. No. 4,134,792); fluorescers (see Clin. Chem. (1979)25:353); chromophores; luminescers such as chemiluminescers and bioluminescers (see (Clin. Chem. (1979)25:512, and ibid, 1531); specifically bindable ligands; proximal interacting pairs; and radioisotopes such as $^3H$, $^{35}S$, $^{32}P$, $^{125}I$, and $^{14}C$. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled antibody can be detected by adding the enzymefor which the label is a cofactor and a substrate for the enzyme. A hapten or ligand (e.g., biotin) labeled antibody can be detected by adding an antibody to the hapten or a protein (e.g., avidin) which binds the ligand, tagged with a detectable molecule. Such detectable molecule can be some molecule with a measurable physical property (e.g., fluorescence or absorbance) or a participant in an enzyme reaction (e.g., see above list). For example, one can use an enzyme which acts upon a substrate to generate a product with a measurable physical property. Examples of the latter include, but are not limited to, $\beta$-galactosidase, alkaline phosphatase and peroxidase. For in situ hybridization studies, ideally the final product is water insoluble. Proximal interacting or linking labels as are known in the immunoassay field (see Clin. Chem. 27:1797(1981) and U.S. Pat. Nos. 3,996,345 and 4,233,402) can be applied to the present method by using two different populations of antibodies, one labeled with one member of the pair and the other labeled with the other of the pair. For instance, a first portion of antibodies to intercalation complexes is labeled with a fluorescer and a second portion is labeled with a quencher. The presence of intercalation complexes is indicated by quenching of fluorescence due to the proximate binding of first and second portion antibodies along the intercalated nucleic acid duplex. Similarly, one can use first and second enzyme labels where the product of one is a substrate for the other. The presence of complexes is then indicated by increased turnover by the second enzyme due to a proximate enzyme channeling effect. Other labeling schemes will be evident to one of ordinary skill in the art.

Alternatively, the antibody can be detected based on a native property such as its own antigenicity. A labeled anti-(antibody) antibody will bind to the primary antibody reagent where the label for the second antibody is any conventional label as above. Further, antibody can be detected by complement fixation or the use of labeled protein A, as well as other techniques known in the art for detecting antibodies.

Where the antibody is labeled, as is preferred, the labeling moiety and the antibody reagent are associated or linked to one another by direct chemical linkage such as involving covalent bonds, or by indirect linkage such as by incorporation of the label in a microcapsule or liposome which is in turn linked to the antibody. Labeling techniques are well-known in the art and any convenient method can be used in the present invention.

REACTION MIXTURE

The test sample to be assayed can be any medium of interest, and will usually be a liquid sample of medical, veterinary, environmental, nutritional, or industrial significance. Human and animal specimens and body fluids particularly can be assayed by the present method, including urine, blood (serum or plasma), milk, cerebrospinal fluid, sputum, fecal matter, lung aspirates, throat swabs, genital swabs and exudates, rectal swabs, and nasopharnygal aspirates. Where the test sample obtained from the patient or other source to be tested contains principally double stranded nucleic acids, such as contained in cells, the sample will be treated to denature the nucleic acids, and if necessary first to release nucleic acids from cells. Denaturation of nucleic acids is preferably accomplished by heating in boiling water or alkali treatment (e.g., 0.1N sodium hydroxide), which if desired, can simultaneously be used to lyse cells. Also, release of nucleic acids can, for example, be obtained by mechanical disruption (freeze/thaw, abrasion, sonication), physical/chemical disruption (detergents such as Triton, Tween, sodium dodecylsulfate, alkali treatment, osmotic shock, or heat), or enzymatic lysis (lysozyme, proteinase K, pepsin). The resulting test medium will contain nucleic acids in single stranded form which can then be assayed according to the present hybridization method.

As is known in the art, various hybridization conditions can be employed in the assay. Typically, hybridization will proceed at slightly elevated temperatures, e.g., between about 35° and 70° C. and usually around 65° C., in a solution comprising buffer at pH between about 6 and 8 and with appropriate ionic strength (e.g., 2XSSC where 1XSSC=0.15M sodium chloride and 0.015M sodium citrate, pH 7.0), protein such as bovine serum albumin, Ficoll (a trademark identifying a copolymer of sucrose and epichlorohydrin sold by Pharmacia Fine Chemicals, Piscataway, NJ), polyvinylpyrrolidone, and a denatured foreign DNA such as from calf thymus or salmon sperm. The degree of complementarity between the sample and probe strands required for hybridization to occur depends on the stringency of the conditions. The extent and specificity of hybridization is affected by the following principal conditions:

1. The purity of the nucleic acid preparation.
2. Base composition of the probe—G-C base pairs will exhibit greater thermal stability than A-T base pairs. Thus, hybridizations involving higher G-C content will be stable at higher temperatures.
3. Length of homologous base sequence—Any short sequence of bases (e.g., less than 6 bases), has a high degree of probability of being present in many nucleic acids. Thus, little or no specificity can be attained in hybridizations involving such short sequences. The present homologous probe sequence will be at least 10 bases, usually 20 bases or more, and preferably greater than 100 bases. From a practical standpoint, the homologous probe sequence will often be between 300–1000 nucleotides.
4. Ionic strength—The rate of reannealing increases as the ionic strength of the incubation solution increases. Thermal stability of hybrids also increases.
5. Incubation temperature—Optimal reannealing occurs at a temperature about 25°–30° C. below the melting temperature (Tm) for a given duplex. Incubation at temperatures significantly below the optimum allows less related base sequences to hybridize.
6. Nucleic acid concentration and incubation time—Normally, to drive the reaction towards hybridization, one of the hybridizable sample nucleic acid or probe nucleic acid will be present in excess, usually 100 fold excess or greater.
7. Denaturing reagents—The presence of hydrogen bond disrupting agents such as formamide and urea increases the stringency of hybridization.
8. Incubation time—The longer the incubation time the more complete will be the hybridization.
9. Volume exclusion agents—The presence of these agents, as exemplified by dextran and dextran sulfate, are thought to effectively increase the concentration of the hybridizing elements thereby increasing the rate of resulting hybridization.

Normally, the antibody reagent, and the intercalator in the case of formats wherein it is added as a free compound, are not present in the hybridization solution, however, this is not precluded where desired and where the hybridization conditions are favorable to antibody binding and intercalation. In the usual case, intercalation complexes associated with hybridized probe are detected after separation of hybridized probe from the hybridization solution. Where intercalator is added as a free compound, its concentration will normally be chosen so as to be sufficient to saturate the intercalation complexes present but not so great that significant, e.g., greater than 10 percent, self-stacking of intercalator occurs. The conditions for intercalation will generally be mild, e.g., at a pH between about 6 and 8, moderate ionic strength ($\leq 1$), room temperature, with no extended incubation necessary, i.e., less than 15 minutes in the usual case.

For detection of intercalation complex, antibody to the complex is added in excess and allowed to incubate for the time required to form a detectable product (e.g., 5 minutes to 24 hours) under conditions of neutral pH (e.g., between 6 and 8), moderate ionic strength ($\leq 1$) and moderate temperature (20°–40° C.). Excess (unbound) antibody is then removed by washing under similar conditions.

It may be necessary or desirable to modify the procedure above by including an intercalator in the washing step to maintain saturation of the nucleic acid-intercalator complex. Also, if desired some or all of the steps above can be combined, such as adding the intercalating agent and antibody simultaneously.

REAGENT SYSTEM

The present invention additionally provides a reagent system, i.e., reagent combination or means, comprising all of the essential elements required to conduct a desired assay method. The reagent system is presented in a commercially packaged form, as a composition or admixture where the compatability of the reagents will allow, in a test device configuration, or more usually as a test kit, i.e., a packaged combination of one or more containers, devices, or the like holding the necessary reagents, and usually including written instructions for the performance of assays. Reagent systems of the present invention include all configurations and compositions for performing the various hybridization formats described herein, particularly the four method types particularly illustrated above and in the drawings.

In all cases, the reagent system will comprise (1) a probe, (2) a nucleic acid intercalator as described herein, and (3) the antibody reagent, preferably labeled with a detectable chemical group also as described herein. The system can additionally comprise a solid support for immobilizing single stranded nucleic acids from the test medium. Alternatively, the probe element can be presented immobilized on such a support. Further, the intercalator can be present in the reagent system as a separate, free compound, substantially uncomplexed with nucleic acids, or can be bound to the probe either in the form of intercalation complexes where the probe comprises a double stranded region, and optionally covalently or otherwise chemically linked to one or both of the strands, or by being chemically linked, e.g., covalently, to a single stranded probe region such that duplex formation in such region results in the formation of intercalation complexes. In the case of the sandwich format, a second probe as described above is included in the system. A test kit form of the system can additionally include ancillary chemicals such as the components of the hybridization solution and denaturation agents capable of converting double stranded nucleic acids in a test sample into single stranded form. Preferably, there is included a chemical lysing and denaturing agent, e.g., alkali, for treating the sample to release single stranded nucleic acid therefrom.

The present invention will now be illustrated, but is not intended to be limited, by the following examples:

EXAMPLES

I. Materials

A. Preparation of tufA probe having a covalently intercalated double stranded portion.

The nucleic acid probe is a modified M13mp9 vector (Messing and Vieria (1982) Gene. 19:269; commercially available from New England Biolabs, Beverly, MA) containing an 800 bp insert between the Hinc II and EcoRI restriction endonuclease sites of RFM13mp9. The 800 base insert is a fragment of the 1,190 base tufA sequence from *E. coli;* and is the portion of the probe (which is comprised of vector and insert) which will actually hybridize to the specimen nucleic acid. It will be referred to as the tufA insert. The modified M13mp9 bacteriophage is denoted M13-10 and is available through the American Type Culture Collection, Rockville, MD (ATCC 39403-B1).

The E. coli base organism used for propagation of M13-10 phage is JM103 [(Δlac pro), supE, thi, strA, endA sbcB, hsdR−, F'traD36, proAB, lacIq, ZΔM15] which is commercially available from Bethesda Research Laboratories, Gaithersburg, MD. E. coli JM103 is transformed with M13-10 DNA, and a culture of JM103 is subsequently infected with the transformed JM103. The single stranded form of M13-10 is isolated from the phage particles excreted into the medium by the infected *E. coli*. The phage particles are harvested and the single stranded M13-10 DNA is isolated following standard procedures [Messing et al (1981) Nucleic Acids Res. 9:309].

Using an oligonucleotide primer complementary to the M13mp9 vector on the 5' terminus of the tufA insert, deoxynucleoside triphosphates and E. coli DNA polymerase (Klenow Fragment), a second DNA strand is synthesized. This second strand is synthesized with limiting quantities of deoxynucleoside triphosphates such that it does not extend to the tufA insert because this insert must remain substantially single stranded for the probe to be useful in a hybridization assay. This technique has been described in the literature [Hu and Messing (1982) Gene 17:271-277] and the oligonucleotide primer (sequence CACAATTCCACACAAC) is commercially available from New England Biolabs, Beverly, MA.

The amount of double stranded DNA present in the M13-10 probe can be estimated by using a radiolabeled nucleoside triphosphate in the second strand synthesis or by $S_1$ nuclease digestion followed by a fluorescence assay with ethidium bromide.

The double stranded region of the M13-10 probe prepared as described above is intercalated and covalently linked with ethidium in a photoaffinity reaction using a photolabeled ethidium derivative, 8-azidoethidium. This photoreactive intercalator is prepared and isolated as described in the literature [Graves et al (1977), Biochim. Biophys. Acta 479:98-104]. Its binding to double stranded DNA has been shown to mimic that of its parent compound, ethidium bromide [Bolton and Kearns (1978) Nucl. Acids. Res. 5:4891; Garland et al (1980) Biochem. 19:3221—our studies indicate that this procedure gives a mixture of 3-azido and 8-azidoethidium isomers]. Because 8-azidoethidium is photoreactive, standard precautions must be taken in handling it to prevent decomposition. Working in the dark in the presence of a red photographic safelight has been found to be satisfactory. Solutions of 8-azidoethidium may be stored frozen in the dark at −70° C. for at least one month.

Photolysis with visible light converts the azido moiety in 8-azidoethidium to a chemically reactive nitrene, which will quickly react with available nucleophiles to form covalent ethidium adducts [Knowles (1971) Acc. Chem. Res. 5:155]. If 8-azidoethidium is intercalated between the base pairs of DNA when photolysis occurs, covalently coupling of ethidium to DNA occurs with high efficiency [Bolton and Kearns (1978) Nucl. Acids Res. 5:4891].

Ethidium is covalently coupled to the double stranded region of M13-10 by photolysis of a solution containing approximately 1 mM DNA base pairs and 0.5 mM 8-azidoethidium in an appropriate buffer such as 20 mM tris-(hydroxymethyl)aminomethane (Tris-HCl), 200 mM sodium chloride (NaCl), pH 8.0. Photolysis is accomplished with a 150 watt outdoor spotlight, with the stirred reaction 5-20 centimeters (cm) away from the light source. To prevent the photolysis reaction from overheating and to block out any short wavelength radiation, i.e., less than 300 nanometers (nm), the photolysis reaction is surrounded by a glass water bath which is connected to a water circulator with temperature regulation. After an appropriate incubation period such as 60 minutes, ethidium groups not covalently bound to DNA are removed by a series, e.g., 10, of successive extractions with an equal volume of water saturated n-butanol. Additional 8-azidoethidium (final concentration in the range of 0.4 mM) is added and the photolysis and extraction steps are repeated. The amount of ethidium associated with the DNA is estimated using extinction coefficient values of $\epsilon_{490} \approx 4 \times 10^3 M^{-1} cm^{-1}$ for photolyzed ethidium azide the relationship between $A_{260}$ and $A_{490}$ for photolyzed ethidium bound to DNA $[A_{260}=(A_{490}\times 3.4)-0.011]$, and $\epsilon_{260} \approx 1.32 \times 10^4 M^{-1} cm^{-1}$ for the concentration of DNA base pairs of a given DNA being labeled. Preferably, the probe is saturated with ethidium such that there is 1 ethidium moiety for every 2 DNA base pairs in the double stranded region of the probe. The photolysis reaction and extractions are repeated until the desired labeling density is obtained.

B. Preparation of adenovirus probes for sandwich hybridization format.

Sandwich hybridization formats are described in the literature—Dunn and Hassell (1977) Cell 12:23; Dunn and Sambrook (1980) Methods in Enzymology 65:468, Ranki et al (1983) Gene 21:77; Ranki et al (1983) Curr. Topics in Microbiology and Immunol. 104:307-310.

This approach requires two nucleic acid probes, each of which is complementary to a unique region of the nucleic acid being tested in a specimen. One of the probes is immobilized on a solid support while the other is labeled in some manner and is initially in solution with the specimen nucleic acids. These will be referred to as the solid and solution phase probes, respectively.

The solid and solution phase probes are prepared from restriction endonuclease digests of DNA from adenovirus type 2 (Ad2) as described by Ranki et al (1980) Gene 21:77-85. The solid phase probe is comprised of BamH1 fragments C or D [Tooze (1980) "The Molecular Biology of Tumor Viruses" (2nd ed) Part 2: DNA Tumor viruses, Cold Spring Harbor Laboratory, Cold Spring Harbor, NY, pp. 933-934] of Ad2 DNA inserted in a pBR322 vector. These probes have been denoted pkTH1201 and pkTH1202, respectively. The solution phase probe is comprised of a BamH1 and BglII restriction endonucleoase digest of pkTH1201 in which fragments are shotgun-cloned into the BamH1 restriction endonuclease site of M13mp7 [Messing et al (1981) Nuc. Acids Res. 9:309]. The modified M13mp7 containing as an insert a fragment of the Ad2 C fragment is designated mkTH2306.

The solution probe mkTH1206 is made partially double stranded as described in Part I-A above and the double stranded region is labeled with an intercalating agent, e.g., ethidium, also as described in Part I-A above.

C. Preparation of HCMV probe.

The EcoRI restriction endonuclease fragment O from human cytomegalovirus (HCMV) strain AD169 [Tamashiro et al (1982) J. Virol., May, 547-556; Chou and Merigan (1983) New Engl. J. of Med. 308:921] is cloned into the pBR322 derivative pACYC184 which is used to transfect E. coli strain HB101 Rec A$^-$ as described by Tamashiro et al. After propagation and purification at the insert-bearing pACYC184, the plasmid is digested with restriction endonuclease EcoRI and the 6.8 kb O fragment of HCMV is purified by preparative electrophoresis in 0.8% agarose gels using standard procedures [Maniatis et al (1982) "Molecular Cloning", Cold Spring Harbor Laboratory, Cold Spring Harbor, NY].

D. Preparation of intercalator-labeled HCMV probe.

The purified double-stranded O fragment from Part I-C above is then covalently labeled with ethidium by using the photolabile ethidium derivative, 8-azidoethidium, as described in Part I-A above.

E. Preparation of intercalation complex immunogen.

Calf thymus or salmon sperm DNA is sheared by repetitive passage through a hypodermic needle, treated with $S_1$ nuclease to remove single stranded regions [Maniatis (1982) "Molecular Cloning", Cold Spring Harbor Laboratory, Cold Spring Harbor, NY] and separated from the resulting nucleotides by any one of a number of standard methods (e.g., ethanol precipitation, gel exclusion chromatograhy, or ion exchange chromatography).

The purified double stranded DNA is then covalently coupled to the photolabile ethidium derivative 8-azidoethidium by photolysis as described in Part I-A above. A carrier protein is prepared by methylation of carboxylic acid residues (Mandell and Hershey (1960) Anal. Biochem. 1:66) then combined with the intercator-labeled DNA to form an electrostatically associated nucleic acid-protein complex as described in Poirier et al (1982) PNAS 79:6443.

F. Preparation of polyclonal antiserum to the intercalation complex.

Polyclonal antiserum against inercalator-DNA complexes is elicited in rabbits using the immunization techniques and schedules described in the literature [Stollar (1980) Methods in Enzymology 70:70]. The antiserum is screened in a solid phase assay similar to that used for monoclonal antibodies, e.g., as described by Lange et al (1976) Clin. Exp. Immunol. 25:191; Pisetsky et al (1981) J. Immun. Methods 41:187. The initial screening criterion would be binding to the intercalator-DNA complex.

The IgG fraction of the antisera containing antibodies is isolated from other serum proteins by ammonium sulfate precipitation followed by chromatography on DEAE cellulose [Livingston (1974) Methods in Enzymology 34:723].

The IgG fraction of the antisera is purified further by affinity chromotography on a column containing a resin on which the DNA-intercalator complex is immobilized [Stollar (1980) Methods in Enzymology 70:70]. After applying the IgG fraction to the column, nonspecifically bound protein is removed by washing, and the specific antibodies eluted with 2M acetic acid in the cold [Stollar (1980) ibid].

The purified antibodies are screened more thoroughly to determine their usefulness in the hybridization assay. The antibodies must bind the intercalator-DNA complex with high affinity (preferably, $K_A \geqq 10^{10} M^{-1}$); cross-reactivity with free intercalator or single stranded DNA is not acceptable. Depending upon the assay format, some cross-reactivity of the antibodies with double stranded DNA is acceptable.

G. Preparation of monoclonal antibodies to the intercalation complex.

Using the intercalator-DNA immunogen prepared as described above, mouse monoclonal antibodies to the intercalator-DNA complex are obtained using standard procedures [Galfre and Milstein (1981) Methods in Enzym. 73:1]. The monoclonal antibodies are screened using a modification of the techniques described in the literature, e.g., Lange et al (1976) Clin. Exp. Immunol. 25:191; Pisctsky et al (1981) J. Immun. Methods 41:187). To be useful in the assay for detection of DNA-intercalator complexes, a monoclonal antibody should bind to the DNA intercalator complex with high affinity (preferably, $K_A \geqq 10^{10} M^{-1}$), but cannot bind to single stranded DNA or free intercalating agent. Cross-reactivity with double stranded DNA may be acceptable in some of the assay formats.

Mouse monoclonal antibody is purified in a two step procedure. The neat ascites fluid is applied to a column of Affi-Gel Blue resin (Bio-Rad Laboratories, Richmond, CA) equilibrated with 10 mM Tris-HCl, 0.15M NaCl, pH 8.0, and eluted with the same buffer. This step removes albumin, which is retained on the column. The final step in the purification is application to DEAE-Sepharose (Pharmacia Fine Chemicals, Piscataway, NJ) and elution with a linear gradient of 10 mM Tris-HCl, pH 8.0, to 10 mM Tris-HCl, 200 mM NaCl. This gives purified mouse monoclonal antibody free from contaminating serum proteins such as albumin and transferrin.

H. Preparation of β-galactosidase-antibody conjugate.

β-galactosidase (30,000 units, grade VIII, commercially available from Sigma Chemical Co., St. Louis, MO) was dissolved in 2 ml of a buffer solution comprised of 0.1M N-2-hydroxyethylpiperazine-N'-2-ethane sulfonic acid (HEPES), 0.09M NaCl, pH 7.0. This gave a β-galactosidase solution containing 37.7 mg of protein (70 nmol) in 1.84 ml. A 3.5 μmol portion (a 50-fold molar excess) of dithiothreitol (DTT) was added to this solution, and the mixture allowed to stand at room temperature for four hours.

DTT was removed from the enzyme solution by chromatographing the mixture on a 2.5×80 cm column of Sepharose 6B.Cl resin (Pharmacia Fine Chemicals, Piscataway, NJ) using as the eluent the HEPES/NaCl buffer described above. Protein-containing fractions were pooled to give a total volume of 15 ml. Using an $E_{280}^{1\%}=20.9$ [Worthington Enzyme Manual (1977), Worthington Biochemical Corporation, Freehold, NJ, p. 195], the β-galactosidase concentration was determined to be 9.62 mg/ml. The number of sulfhydryl groups on the enzyme was determined to be 11.0 using Ellman's reagent [Ellman (1959) Arch. Biochem. Biophys. 82:70]. Typically this protocol gives 9-15 free sulfhydryl groups per β-galactosidase molecule.

The heterobifunctional coupling reagent succinimidyl-4-(N-maleimidomethyl)cyclohexane-1-carboxylate (SMCC, available from Pierce Chemical Co., Rockford, IL) was used to couple β-galactosidase to an antibody. This coupling reagent contains a maleimido group which selectively reacts with sulfhydryl moieties and an N-hydroxysuccinimide ester for coupling to amino groups. The coupling procedure is comprised of two steps: reacting SMCC with antibody amino groups followed by coupling the derivatized antibody to β-galactosidase by reaction of the maleimido moiety with β-galactosidase sulfhydryl groups.

A 5.3 mg portion of SMCC was dissolved in 250 μl of anhydrous N,N-dimethylformamide (DMF). The actual concentration of reactive maleimide groups in this solution was determined by reaction with a known quantity of glutathione, followed by determining the quantity of glutathione sulfhydryl groups using Ellman's reagent (ibid). For example, 40 μl of the DMF solution was diluted to 3 ml with HEPES/0.015M NaCl buffer. A 25 μl volume of this aqueous solution of SMCC solution was then combined with 825 μl HEPES/NaCl buffer and 100 μl of 1 mM glutathione. After standing at room temperature for 15 minutes, the amount of unreacted glutathione was determined using Ellman's reagent (ibid) and the appropriate standards (i.e., unreacted glutathione and a blank with no glutathione). Several determinations were made for each SMCC solution, and their results averaged. This protocol indicated that the DMF solution of SMCC prepared as described above was 52 mM in reactive maleimide groups.

A 6.0 mg (40 μmol) portion of a mouse monoclonal antibody was combined with 400 μmol of SMCC in a final volume of 533 μl of HEPES/0.15M NaCl and allowed to react 1 hour at 30° C. The reaction mixture was then applied to a 1×24 cm column of Bio-Gel P-2 resin (Bio-Rad Laboratories, Richmond, CA) and eluted with HEPES/0.15M NaCl. All protein containing fractions were pooled; the protein concentration was determined using the method of Sedmack and Grossberg [Anal. Biochem. 79:544(1977)] and the number of maleimide groups were determined as described above. These determinations indicated an antibody concentration of 1.98 mg/ml, with 1-2 maleimides/antibody molecule.

A 28 mg portion of the antibody-maleimide conjugate was combined with 10 mg of DTT-treated β-galactosidase (final volume 2.45 μl) and allowed to react 4 hours at room temperature. The mixture was then applied to a 2.5×80 cm column of Sepharose 6B.Cl (Pharmacia, Piscataway, NJ) and eluted with HEPES/0.15M NaCl at 4° C. The flow rate was 4 ml/hr; 3 ml fractions were collected. Fractions were assayed for β-galactosidase activity and antibody binding capacity. Fractions 39-42 had both properties and were pooled.

J. Preparation of biotin-labeled antibodies.

Purified antisera is treated with the N-hydroxysuccinimide ester of biotin (commercially available from Sigma Chemical Co., St. Louis, MO or Biosearch, San Rafael, CA) using the methods described in the literature [Oi et al (1982), J. Cell. Biol. 93:981; Heitzmann et al (1974) Proc. Natl. Acad. Sci. USA 71:3537; Green (1975) Adv. Protein Chem. 29:85].

K. Preparation of radiolabelled antibodies.

Purified antibody is radiolabeled following procedures given in the literature. Radioiodination is accomplished by reaction of the antibodies with $^{125}$I-labeled 3-(4-hydroxyphenyl)propionic acid N-hydroxysuccinimide ester (commercially available from New England Nuclear, Boston, MA) following the protocol of Bolton and Hunter [Biochem. J. 133:529 (1973)]. Alternatively, the antibody fraction is covalently coupled with a bifunctional chelating agent [Yeh et al (1979) Anal. Biochem. 100:152] and is subsequently labeled with an appropriate radioactive metal ion. This latter approach has the advantage that the shelf life of the antibody fraction is not limited by the half life of a radioisotope.

L. Preparation of alkaline phosphatase-biotin-avidin complex

An alkaline phosphatase-biotin-avidin complex is prepared as described by Leary et al [Proc. Natl. Acad. Sci. USA 80:4045 (1983)] Calf intestinal alkaline phosphatase is first cross-linked by reaction with disuccimidyl suberate, then coupled with the N-hydroxysuccinimide ester of biotinyl-ε-aminocaproic acid. After purification, the alkaline phosphatase-biotin complex is labeled with avidin (which has 4 biotin binding sites/avidin molecule) by combining the alkaline phosphatase-biotin complex with a slight molar excess of avidin. Either avidin or a bacterial analog of avidin, steptavidin [Hofmann et al (1980) Proc. Natl. Acad. Sci. USA 77:4666–4668; commercially available from Bethesda Research Laboratories, Gaithersburg, MD] may be used in this last step.

The detection system used for the alkaline phosphatase-biotin-avidin complex is comprised of nitro blue tetrazolium and 5-bromo-4-chloro-3-indolyl phosphate as described by Leary et al (ibid).

II. Methods

A. Detection of gram negative bacteria in urine—(Method Type 1) solid-phase, sample immobilized, hybridization assay with tufA probe having a covalently intercalated double stranded region, monitored with enzyme-labeled antibody (see FIG. 2).

Because its sequence is highly conserved, the tufA sequence from E. coli can be used to detect the presence of gram negative bacteria in urine specimens. Clinical urine samples are clarified by centrifugation for a short period of time (e.g., 5 min.) at a low centrifugal force (e.g., 8000 rpms with a Sorvall GLC-3 centrifuge). Bacterial cells in the supernatant are lysed and the bacterial genome is denatured by making the urine specimen 0.5M in sodium hydroxide (NaOH) for 10 minutes at an elevated temperature (65° C.). Alternatively, this may be done by heating the urine to 90° C. and maintaining that temperature for 10 minutes. After lysis and denaturation, the urine sample is diluted and neutralized with an equal volume of 20XSSPE (3.6M NaCl, 0.2M $NaPO_4$, 20 mM EDTA, pH 7.7). The urine specimen is then immediately filtered through a nitrocellulose membrane under mild vacuum. The immobilized bacterial DNA is then fixed to the nitrocellolose membrane by baking in vacuo at 80° C. for 2 hours. The filter containing the immobilized specimen DNA is treated with prehybridization solution [0.1% (w/v) each Ficoll (Pharmacia), polyvinylpyrrolidone and BSA in 5XSSPE, 100–200 μg/ml denatured, heterologous DNA] for 1–3 hours at 65° C. A 50–100 μl volume of prehybridization solution/$cm^2$ of filter is used. After prehybridization treatment, the ethidium labeled probe prepared as described in Part I-A above is added to the prehybridization solution and hybridization is allowed to occur (1–72 hours). The above are all standard techniques found in the literature [Maniatis et al (1982) "Molecular Cloning", Cold Spring Harbor Laboratory, Cold Spring Harbor, NY].

After the hybridization, the filter is washed to remove excess probe DNA. The filter is then immersed into a solution containing β-galactosidase-labeled antibodies to the intercalator-DNA complex and incubated for 5 minutes to 12 hours. Excess antibody is removed by washing, and the amount of β-galactosidase associated with the filter is determined by adding a fluorogenic substrate of the enzymes (e.g., 4-methylumbelliferone β-galactoside) and measuring fluorescence intensity after a period of time. Because the quantity of enzyme present is likely to be quite low, the fluorogenic substrate is added in a concentration greater than or equal to its Michaelis constant (Km) for β-galactosidase. Standards, with a defined quantity of probe immobilized on the filter, can be run simultaneously so that hybridization can be quantitated.

B. Detection of adenovirus-(Method Type 2) sandwich hybridization assay with labeled probe having a covalently intercalated double stranded region, monitored with enzyme-labeled antibody (see FIG. 3).

This method is based on the sandwich hybridization assay described by Ranki et al for the detection of adenovirus type 2 (Ad2) DNA in clinical samples [Ranki et al (1983) Gene 21:77; Ranki et al (1983) Current Topics in Microbiology and Immunology 104, Springer-Verlag, NY p. 307]. The solid phase probe pKTH1202 (see Part I-B above) is denatured, nicked and immobilized on nitrocellulose filters. After fixation (baking in vacuo at 80° C. for 2 hours), the filters are treated with a prehybridization solution for one hour at 65° C. DNA from clinical specimens and the intercalator-labeled solution hybridization probe mkTH1206 (prepared as described in Part I-B above) are added to the prehybridization solution and hybridization of the probes with the specimen DNA is allowed to occur for 1–72 hours. After hybridization, excess solution probe (mkTH1206) is removed by washing.

The extent of hybridization is quantitated using β-galactosidase-labeled antibody to the intercalator-DNA complex as outlined in Part II-A above.

C. Detection of human cytomegalovirus in urine (Method Type 3) solid-phase, probe immobilized hybridization assay, monitored with biotin-labeled antibodies and enzyme-labeled avidin (see FIG. 4).

This method is used for the detection of human cytomegalovirus (HCMV) in clinical urine specimens. The purified probe (EcoR1 O fragment of HCMV strain AD169, as described in Part I-C above) is denatured by heating at 90° C. for 10 minutes, rapidly chilled on ice (to prevent renaturation) and combined with an equal volume of 20XSSPE (3.6M NaCl, 0.2M $NaPO_4$, 20 mM EDTA, pH 7.7). The single stranded probe DNA is then immobilized and fixed on a nitrocellulose membrane using standard procedures. The membrane is then treated with a prehybridization solution, preferably one not containing heterologous DNA. One prehybridization solution which can be used is that described by New England Nuclear for their Gene Screen Plus ™ membranes; this solution is comprised of 1% SDS, 1M NaCl, and 10% dextran sulfate. To prevent nonspecific binding of the antibody in the final steps of the detection schemes, it may be desirable to include BSA in the prehybridization solution.

The clinical urine specimen to be tested is prepared in a manner similar to that described by Chou and Merigan [New Engl. J. Med. 308:921 (1983)]. After clarification of the sample and concentration of the HCMV phage particles by centrifugation, they are resuspended in a minimum volume of 0.5M NaOH and allowed to stand for 15 minutes. After neutralization with a minimum volume of 20XSSPE, the denatured clinical specimens are added to the filter in 1% SDS, 1M NaCl, 10% dextran sulfate and 100 μg/ml denatured salmon sperm DNA. Hybridization is allowed to proceed at 65° C. for 1–72 hours; the filters are then washed in 2XSSPE.

The filters are immersed in a minimum volume of a solution containing the selected intercalator (e.g., ethidium bromide at a submillimolar concentration). Biotinylated antibody to the DNA-intercalator complex (Part I-J above) is then added and allowed to bind (1–24 hours). Excess antibody is removed by washing. In some situations it may be necessary to include the intercalating agent in these wash steps to keep the double-stranded DNA saturated.

A streptavidin-biotin-alkaline phosphatase complex (Part I-L above) is then added and allowed to bind to the biotinylated antibody associated with the DNA as described by Ward et al [Proc. Natl. Acad. Sci. USA 80:4045(1983)]. After washing away excess alkaline phosphatase conjugates, the presence of conjugate associated with the filter is determined by adding a colorimetric substrate for alkaline phosphatase as described by Ward (ibid). This is a direct measure of the presence of HCMV DNA in the clinical urine specimen.

D. Detection of human cytomegalovirus in urine (Method Type 4) solid-phase, intercalator-labeled-probe immobilized hybridization assay, monitored with radiolabeled second antibody to intercalation complex antibody (see FIG. 5).

This method is similar to that of Part II-C above except that the probe is already labled with intercalating agent, and the final step of the detection scheme requires a second, isotopically labeled antibody.

The probe, ethidium labeled Eco RI fragment O of HCMV (prepared as described in Part I-D above) is denatured, immobilized and fixed on a nitrocellulose support as described for the method of Part II-C above. Viral DNA is isolated from urine samples, denatured, and hybridized to the immobilized probe also as described in Part II-C above, except that addition of free intercalator is unnecessary.

After washing the filter with the hybridized DNA, excess mouse monoclonal antibody to the intercalator-DNA complex (see Part I-G above) is added and allowed to bind to the hybridized DNA intercalator complex (30 minutes to 6 hours). Excess mouse antibody is removed by washing and excess radiolabeled rabbit-anti(mouse IgG) (Part I-K) is added. After a 30 minute to 6 hour incubation, excess antibody is again removed by washing. Hybridization is quantititated by autoradiography or gamma counting.

III. Demonstration of Antigenicity of Intercalation Complexes

A. Preparation of covalent ethidium-DNA complexes

About 250 mg of salmon sperm DNA (Sigma Chemical Co., St. Louis, MO) is dissolved in 40 ml of 50 mM NaCl and sheared by five passages through a 23 gauge needle. The sheared DNA is placed in a 250 ml flask and diluted with an additional 160 ml of buffer. One hundred forty-five microliters (145 $\mu$l) of $S_1$-nuclease, 200,000 units per ml (Pharmacia P-L Biochemicals, Piscataway, NJ), is added and the mixture is incubated at 37° C. for 50 minutes.

Then the reaction mixture is extracted twice with phenol:chloroform, once with chloroform and the DNA is precipitated twice with ethanol [Maniatis et al (1982) "Molecular Cloning", Cold Spring Harbor Laboratory, Cold Spring Harbor, NY]. The final precipitate is dissolved in 70 ml of 20 mM Tris hydrochloride buffer, pH 8.0.

This DNA is reacted wwith 8-azidoethidium under the following conditions. The reaction mixture is prepared with 33 ml of 2.7 mg DNA/ml, 13.5 ml of 4.95 mM 8-azidoethidium, 13.5 ml of 0.2M Tris-hydrochloride buffer, pH 8.0, 0.2M NaCl, and 76 ml water. The mixture is placed in a 250 ml beaker with a water jacket maintained at 22° C. The mixture is stirred and illuminated for 60 minutes by a 150 watt spotlight at a distance of 10 cm. This photolysis is repeated with an identical reaction mixture.

The photolyzed reaction mixtures are combined and extracted 10-times with an equal volume each time of n-butanol saturated with 20 mM Tris-hydrochloride buffer, pH 8.0, 0.2M NaCl. The extracted DNA solution is combined with 23 ml of 4.95 mM 8-azidoethidium and 77 ml of 20 mM Tris-hydrochloride buffer, pH 8.0, 0.2M NaCl. This solution is stirred in the water-jacketed beaker and photolyzed for 90 minutes. The reaction products are extracted 10 times with buffer saturated butanol as described above and the DNA is precipiated with ethanol. The precipitate is dissolved in 10 mM Tris-hydrochloride buffer, pH 8.0, 1 mM EDTA and the absorbances at 260 and 490 nm are recorded. Calculations made as described in Example 1A above indicate 1 ethidium residue is incorporated per 4.5 DNA base pairs.

B. Preparation of methylated thyroglobulin

One hundred milligrams of bovine thyroglobulin (Sigma Chemical Co., St. Louis MO) is combined with 10 ml of anhydrous methanol and 400 $\mu$l of 2.55M HCl in methanol. This mixture is stirred on a rotary mixer at room temperature for 5 days. The precipitate is collected by centrifugation and washed twice with methanol and twice with ethanol. Then it is dried under vacuum overnight. About 82 mg of dry powder is obtained.

C. Preparation of covalent ethidium-DNA methylated thyroglobulin complex

Fifty milligrams (55 mg) of methylated thyroglobulin is dissolved in 10 ml of water and 11.3 ml of a 2.2 mg/ml covalent ethidium DNA solution is added. A precipitate forms immediately and the suspension is diluted with 5.0 ml of 1.5M NaCl and 24.6 ml water.

D. Immunization of rabbits

Two milliliters (2 ml) of a mixture composed of 2.5 ml of the covalent ethidium-DNA methylated thyroglobulin complex, 2.5 ml of 0.15M saline and 5.0 ml of complete Freunds adjuvant is injected into four subcutaneous sites on a New Zealand white rabbit. Three weeks later a similar immunization with incomplete Freunds adjuvant is administered followed by additional immunizations at 4 week intervals. Fourteen weeks after the initial immunization, blood is collected for preparation of antiserum.

E. Titration of antibody to ethidium-DNA

Antiserum to covalent ethidium-DNA is titered by an enzyme label immunosorbant assay. Polynucleotides are adsorbed onto the walls of polystyrene microtiter plates and then the rabbit antibody is allowed to bind. Finally the antibody is detected with peroxidase labeled goat anti-rabbit IgG.

Fifty microliter (50 $\mu$l) aliquots of solutions containing 5 $\mu$g of polynucleotide per ml in 15 mM sodium citrate, pH 7.0, 0.15M NaCl is dispensed into wells of Immulon II microtiter plates (Dynatek, Alexandria, VA) and shaken gently at room temperature for 2 hours. Then the wells are emptied and washed with 10 mM sodium phosphate buffer, pH 7.4, 0.15M NaCl, 0.5% bovine serum albumin and 0.5% Tween 20 (PBS/BSA/Tween).

Rabbit antiserum is diluted into 10 mM sodium phosphate, pH 7.4, 0.15M NaCl, 0.5% BSA and 50 $\mu$l aliquots are added to the wells and allowed to stand for 30 minutes. The wells are washed three times with PBS/BSA/Tween. Peroxidase covalently coupled to goat-antirabbit IgG (Cappel Laboratories, Cochranville, PA) is diluted 500-fold in 10 mM sodium phosphate, pH 7.4, 0.15M NaCl, 0.5% BSA and 50 $\mu$l aliquots are added to each well. This solution is allowed to stand in the wells for 30 minutes at room temperature and then the wells are washed three times with PBS/BSA/Tween.

One hundred micromolar (100 μM) ethidium bromide is included in the diluted antiserum of wells containing noncovalent ethidium-DNA complex and the ethidium control wells. All wash solutions and reagents described above for processing these wells contain 100 μM ethidium.

A peroxidase substrate solution is prepared with:
20 mg o-phenylenediamine
5 ml 0.5M $NaHPO_4$
12 ml 0.1M sodium citrate
13 ml water
20 μl 30% hydrogen peroxide Seventy-five microliters (75 μl) of substrate solution is added per well and allowed to react for 10 minutes at room temperature. The reactions are quenched by addition of 50 μl of 2.5M sulfuric acid. Then the absorbances at 488 nm are recorded with a Artek Model 210 microliter plate photometer (Dynatek, Alexandria, VA).

Normal rabbit serum is used as a control and is processed as described for the rabbit antiserum.

F. Results

The results are given in Table A and show that antibody in the control rabbit serum does not bind at significant levels to any of the coated or uncoated wells. It might have a weak antibody titer to single stranded DNA.

The antiserum to the covalent ethidium-DNA has very high titer to the covalent ethidium-DNA. Part of these antibodies are probably binding to ethidium residues that are coupled covalently to the phosphate ribose chain. This conclusion is based on the observation that the titers to the noncovalent ethidium-DNA complex are much lower (see Table A).

These results demonstrate that antibodies can be raised to the ethidium-DNA intercalation complex which do not crossreact significantly with native single or double stranded nucleic acid.

TABLE A

| Dilution | Absorbances (488 nm) | | | | | |
|---|---|---|---|---|---|---|
| | Buffer Control | Covalent Ethidium-DNA | Double-strand DNA | Noncovalent Ethidium-DNA | Ethidium Control | Single-strand DNA |
| Antiserum | | | | | | |
| 50 | 0.067 | >1.2 | 0.126 | 0.825 | 0.049 | 0.283 |
| 200 | 0.032 | >1.2 | 0.068 | 0.597 | 0.021 | 0.184 |
| 800 | 0.022 | >1.2 | 0.067 | 0.30 | 0.016 | 0.174 |
| Control Serum | | | | | | |
| 50 | 0.038 | 0.053 | 0.091 | 0.031 | 0.023 | 0.245 |
| 200 | 0.025 | 0.044 | 0.082 | 0.016 | 0.017 | 0.181 |
| 800 | 0.017 | 0.034 | 0.054 | 0.015 | 0.016 | 0.190 |

Notes:
(1) The buffer control does not contain DNA on the wells.
(2) Double-stranded DNA contains calf thymus DNA on the wells.
(3) Noncovalent ethidium-DNA has calf thymus double-stranded DNA on the wells and 100 μM ethidium in the reagent and wash solutions.
(4) Ethidium control does not have DNA on the wells but has 100 μM ethidium in the reagent and wash solutions.
(5) The single-stranded DNA has heat denatured calf thymus DNA coated on the wells.

The present invention has been particularly described and exemplified above. Obviously, many other variations and modifications of the invention may be made without departing from the spirit and scope hereof.

What is claimed is:

1. A method for detecting a particular polynucleotide sequence in a test medium containing single stranded nucleic acids, comprising the steps of:
   (a) combining the test medium with (i) a nucleic acid probe comprising at least one single stranded base sequence which is substantially complementary to hybridization between the sequence to be detected and the complementary sequence in the probe, and (ii) a nucleic acid intercalator capable of binding to double stranded nucleic acid in the form of intercalation complexes, and
   (b) detecting hybridized probe by adding an antibody, or a fragment thereof, capable of binding with intercalation complexes in the hybridization product resulting from step (a), and determining the antibody or fragment thereof which becomes bound to such complexes.

2. The method of claim 1 wherein the intercalator is combined with the test medium as a separate, free compound and noncovalently binds with double stranded nucleic acid to form intercalation complexes.

3. The method of claim 1 wherein the intercalator is chemically linked to the probe in the single stranded complementary region of the probe, whereby upon hybridization said intercalation complexes are formed in such region.

4. The method of claim 1 wherein the antibody or fragment thereof is labeled with a detectable chemical group.

5. The method of claim 4 wherein the detectable chemical group is an enzymatically active group, a fluorescer, a chromophore, a luminescer, a specifically bindable ligand, or a radioisotope.

6. The method of claim 1 according to a solid phase hybridization technique wherein one of the probe and the single stranded nucleic acids from the test medium is immobilized on a solid support and wherein the antibody associated with the solid support is determined.

7. The method of claim 1 according to a solid phase sandwich hybridization technique wherein the test medium is combined with first and second nucleic acid probes each comprising at least one single stranded base sequence which is substantially complementary to a mutually exclusive portion of the sequence to be detected and wherein one of the probes is immobilized on a solid support.

8. The method of claim 1 according to a solution phase hybridization technique wherein the probe comprises a binding site for a binding substance and wherein after the hybridization step there is added an immobilized form of such binding substance.

9. The method of claim 8 wherein the probe comprises a biotin or hapten moiety and the binding substance is avidin or an anti-hapten antibody, respectively.

10. The method of claim 1 wherein the probe additionally comprises a double stranded portion which, upon addition of the intercalator in step(a) as a separate, free compound, forms said intercalation complexes.

11. The method of claim 1 wherein the intercalator is selected from acridine dyes, phenanthridines, phenazines, furocoumarins, phenothiazines and quinolines.

12. A solid-phase hybridization method for detecting a particular polynucleotide sequence in a liquid test medium containing single stranded nucleic acids, comprising the steps of:
  (a) forming a reaction mixture by contacting the liquid test medium with a nucleic acid probe comprising at least one single stranded base sequence which is substantially complementary to the sequence to be detected, one of the probe and the single stranded nucleic acids from the test medium being immobilized on a solid support, such contact being performed under conditions favorable to hybridization between the sequence to be detected and the complementary probe sequence,
  (b) contacting the solid support carrying resulting immobilized duplexes with a nucleic acid intercalator and an antibody, or fragment thereof, capable of binding with intercalation complexes comprising double stranded nucleic acid complexed with the intercalator,
  (c) separating the solid support carrying resulting immobilized antibody or fragment thereof from the remainder of the reaction mixture, and
  (d) determining the separated antibody or fragment thereof on the solid support as an indication of the presence of the sequence to be detected in the liquid test medium.

13. The method of claim 12 wherein prior to step (b) the solid support carrying immobilized duplexes resulting from step(a) is separated from the remainder of the reaction mixture.

14. The method of claim 12 wherein the antibody or fragment thereof is labeled with a detectable chemical group and wherein in step(d) such detectable group is measured on the solid support as an indication of the presence of the sequence to be detected.

15. The method of claim 12 wherein the probe also comprises at least one double stranded region which, upon addition of the intercalator in step(b), forms said intercalation complexes capable of being bound by the antibody or fragment thereof.

16. The method of claim 12 wherein the liquid test medium comprises a biological sample which has been subjected to conditions to release and denature nucleic acids present therein.

17. A solid-phase hybridization method for detecting a particular polynucleotide sequence in a liquid test medium containing single stranded nucleic acids, comprising the steps of:
  (a) forming a reaction mixture by contacting the liquid test medium with a nucleic acid probe, the probe comprising at least one single stranded base sequence substantially complementary to the sequence to be detected and the probe being chemically linked to a nucleic acid intercalator in the single stranded complementary region of the probe such that duplex formation in such region bearing the linked intercalator results in the formation of intercalation complexes, one of the probe and the single stranded nucleic acids from the test medium being immobilized on a solid support, such contact being performed under conditions flavorable to hybridization between the sequence to be detected and the complementary probe sequence,
  (b) adding to the reaction mixture an antibody, or a fragment thereof, capable of binding with intercalation complexes comprising double stranded nucleic acid complexed with the intercalator,
  (c) separating from the remainder of the reaction mixture, the solid support carrying resulting immobilized antibody or fragment thereof bound to intercalation complexes formed between the intercalator-linked probe and the sequence to be detected, and
  (d) determining the separated antibody or fragment thereof on the solid support as an indication of the presence of the sequence to be detected in the liquid test medium.

18. The method of claim 17 wherein the antibody or fragment thereof is labeled with a detectable chemical group and wherein in step(d) such detectable group is measured on the solid support as an indication of the presence of the sequence to be detected.

19. The method of claim 17 wherein the liquid test medium comprises a biological sample which has been subjected to conditions to release and denature nucleic acids present therein.

20. A solution-phase hybridization method for detecting a particular polynucleotide sequence in a liquid test medium containing single stranded nucleic acids, comprising the steps of:
  (a) forming a reaction mixture by contacting the liquid test medium with a nucleic acid probe comprising at least one single stranded base sequence which is substantially complementary to the sequence to be detected, the probe comprising a binding site for a binding substance, such contact being performed under conditions favorable to hybridization between the sequence to be detected and the complementary probe sequence,
  (b) adding to the reaction mixture simultaneously or in separate steps (i) a nucleic acid intercalator, (ii) an antibody, or fragment thereof, capable of binding with intercalation complexes comprising double stranded nucleic acid complexed with the intercalator, and (iii) an immobilized form of a binding substance for the probe,
  (c) separating the resulting immobilized phase comprising antibody, or fragment thereof, bound to immobilized intercalation complexes from the remainder of the reaction mixture, and
  (d) determining the separated immobilized antibody, or fragment thereof, as an indication of the presence of the sequence to be detected in the liquid test medium.

21. The method of claim 20 wherein the antibody or fragment thereof is labeled with a detectable chemical group and wherein in step(d) such detectable group is measured in the immobilized phase as an indication of the presence of the sequence to be detected.

22. The method of claim 20 wherein the probe comprises a biotin or hapten moiety and the immobilized binding substance is avidin or an anti-hapten antibody, respectively.

23. The method of claim 20 wherein the liquid test medium comprises a biological sample which has been subjected to conditions to release and denature nucleic acids present therein.

24. A test kit for detecting a particular polynucleotide sequence in a test medium, comprising in a packaged combination:
  (1) a nucleic acid probe comprising at least one single stranded base sequence which is substantially complementary to the sequence to be detected,
  (2) a nucleic acid intercalator, and
  (3) an antibody, or a fragment thereof, capable of binding with intercalation complexes comprising hybridized double stranded nucleic acid complexed with the intercalator.

25. The test kit of claim 24 wherein the antibody or fragment thereof is labeled with a detectable chemical group.

26. The test kit of claim 25 wherein the detectable chemical group is an enzymatically active group, a fluorescer, a chromophore, a luminescer, a specifically bindable ligand, or a radioisotope.

27. The test kit of claim 25 wherein the detectable chemical group is an enzyme.

28. The test kit of claim 24 which additionally comprises a solid support for immobilizing single stranded nucleic acids from the test medium.

29. The test kit of claim 24 wherein the probe is immobilized on a solid support.

30. The test kit of claim 24 wherein the probe comprises a binding site for a binding substance and the reagent system additionally comprises an immobilized form of such binding substance.

31. The test kit of claim 30 wherein the probe comprises a biotin or hapten moiety and the immobilized binding substance is avidin or an anti-hapten antibody, respectively.

32. The test kit of claim 24 wherein the intercalator is a separate, free compound, substantially uncomplexed with nucleic acids.

33. The test kit of claim 32 wherein the probe additionally comprises at least one double stranded region.

34. The test kit of claim 24 wherein the intercalator is chemically linked to a single stranded region of the probe such that duplex formation in such region results in the formation of intercalation complexes.

35. The test kit of claim 24 for use in a sandwich hybridization format which comprises a second nucleic acid probe, the first and second probes respectively comprising at least one single stranded base sequence which is substantially complementary to a mutually exclusive portion of the sequence to be detected.

36. The test kit of claim 35 wherein one of the probes is immobilized.

37. The test kit of claim 36 wherein a single stranded region of the probe that is not immobilized is chemically linked to the intercalator such that duplex formation in such region results in the formation of intercalation complexes.

38. The test kit of claim 24 wherein the intercalator is selected from acridine dyes, phenanthridines, phenazines, furocoumarins, phenothiazines and quinolines.

39. The test kit of claim 24 which additionally comprises a denaturation agent capable of converting double stranded nucleic acids in a test sample into single stranded form.

40. A method for detecting double stranded nucleic acid in a liquid medium, comprising the steps of:
  (a) adding to said medium (i) a nucleic acid intercalator and (ii) an antibody, or a fragment thereof, capable of binding with intercalation complexes comprising double stranded nucleic acid complexed with the intercalator, and
  (b) detecting the binding of said antibody or fragment thereof to said complex.

41. The method of claim 40 wherein the antibody or fragment thereof is labeled with a detectable chemical group.

42. The method of claim 41 wherein the detectable chemical group is an enzymatically active group, a fluorescer, a chromophore, a luminescer, a specifically bindable ligand, or a radioisotope.

43. The method of claim 40 wherein the intercalator is selected from acridine dyes, phenanthridines, phenazines, furocoumarins, phenothiazines and quinolines.

* * * * *